United States Patent
Kim et al.

(10) Patent No.: US 11,734,970 B2
(45) Date of Patent: Aug. 22, 2023

(54) DEVICE AND METHOD FOR RECORDING IMAGE FOR VEHICLE

(71) Applicants: Hyundai Motor Company, Seoul (KR); Kia Corporation, Seoul (KR)

(72) Inventors: Gyun Ha Kim, Incheon (KR); Eung Hwan Kim, Seoul (KR); Sang Kyung Seo, Seoul (KR); Dae Yun An, Anyang-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 72 days.

(21) Appl. No.: 17/489,292

(22) Filed: Sep. 29, 2021

(65) Prior Publication Data

US 2022/0172527 A1    Jun. 2, 2022

(30) Foreign Application Priority Data

Nov. 27, 2020    (KR) .......................... 10-2020-0163220

(51) Int. Cl.
*G07C 5/08* (2006.01)
*A61B 5/18* (2006.01)
(Continued)

(52) U.S. Cl.
CPC .............. *G07C 5/0866* (2013.01); *A61B 5/18* (2013.01); *B60W 40/08* (2013.01); *G06V 20/56* (2022.01); *G06V 20/597* (2022.01); *B60W 2040/0872* (2013.01); *B60W 2540/21* (2020.02); *B60W 2540/221* (2020.02)

(58) Field of Classification Search
CPC ...... G07C 5/0866; G07C 5/0841; G07C 5/02; G07C 5/0858; A61B 5/18; B60W 40/08; B60W 2040/0872; B60W 2540/21; B60W 2540/221; G06V 20/56; G06V 20/597; G10L 17/12

See application file for complete search history.

(56) References Cited

U.S. PATENT DOCUMENTS

| 10,322,728 B1 * | 6/2019 | Porikli ................... G06V 10/80 |
| 2003/0154009 A1 * | 8/2003 | Basir .................... G07C 5/0866 |
| | | 348/148 |
| 2008/0167757 A1 * | 7/2008 | Kanevsky .............. G07C 5/085 |
| | | 701/1 |

OTHER PUBLICATIONS

Kim, Jung Yong, et al., "Assessment of Driver's Emotional Stability by Using Bio-signals," Journal of the Ergonomics Society of Korea, vol. 30, No. 1, Ergonomics Society of Korea, pISSN: 1229-1684, Feb. 28, 2011, pp. 203-211.

(Continued)

*Primary Examiner* — Farzana Hossain
(74) *Attorney, Agent, or Firm* — Slater Matsil, LLP (57) ABSTRACT

An embodiment device for recording an image for a vehicle includes an image acquisition device configured to acquire an image of a region around the vehicle, a sensor device configured to acquire a bio-signal of a driver, the bio-signal comprising a signal carrying information selected from the group consisting of a heart rate, an electrocardiogram, a galvanic skin response (GSR), a body temperature, a voice, a facial expression, and a stress level and combinations thereof, and a controller configured to determine sections of the acquired image to be stored in a non-volatile memory based on the bio-signal and store images of the sections in the non-volatile memory.

20 Claims, 7 Drawing Sheets

| NO. | ITEM | ITEM | TIME | AMOUNT OF CHANGE | SCORE |
|---|---|---|---|---|---|
| 1 | BIO-SIGNAL | A.HEART RATE | WITHIN LAST 5 SECONDS | INCREASED BY EQUAL TO OR MORE THAN 30 BPM | 30 |
| | | | | INCREASED BY RANGE BETWEEN 20 AND 30 BPM | 20 |
| | | | | INCREASED BY RANGE BETWEEN 10 AND 20 BPM | 10 |
| 2 | | B.GSR | WITHIN LAST 5 SECONDS | INCREASED | 15 |
| 3 | | C.BODY TEMPERATURE | WITHIN LAST 5 SECONDS | INCREASED BY EQUAL TO OR MORE THAN 1℃ | 10 |
| | | | | INCREASED BY RANGE OF 0.5 AND 1 ℃ | 5 |
| 4 | | D.VOICE | WITHIN LAST 3 SECONDS | dB INCREASE, SPECIFIC WORD MENTIONED | 10 |
| 5 | | E.FACIAL EXPRESSION | WITHIN LAST 3 SECONDS | SURPRISE, ANGER, ANNOYANCE | 10 |
| 6 | | F.STRESS | WITHIN LAST 5 SECONDS | STRESS LEVEL CHANGE | 5 |
| 7 | VEHICLE SIGNAL | G.WHETHER VEHICLE HAS DEVIATED LINE | WITHIN LAST 1 SECOND | SENSING THAT VEHICLE HAS DEVIATED LINE | 5 |
| 8 | | H.VEHICLE SPEED | WITHIN LAST 1 SECOND | DECREASED BY EQUAL TO OR MORE THAN 30KM/H | 20 |
| | | | | DECREASED BY RANGE BETWEEN 20 AND 30KM/H | 15 |
| | | | | DECREASED BY RANGE BETWEEN 10 AND 20KM/H | 10 |
| 9 | | I.STEERING WHEEL ANGLE | WITHIN LAST 1 SECOND | MANIPULATED BY EQUAL TO OR MORE THAN 30° | 15 |
| | | | | MANIPULATED BY RANGE BETWEEN 20 AND 30° | 10 |
| | | | | MANIPULATED BY RANGE BETWEEN 10 AND 20° | 5 |

(51) Int. Cl.
*B60W 40/08* (2012.01)
*G06V 20/56* (2022.01)
*G06V 20/59* (2022.01)

(56) References Cited

OTHER PUBLICATIONS

Shin, Euiseob, et al., "Driver's Status Recognition Using Multiple Wearable Sensors," KIPS Transactions on Computer and Communication Systems, vol. 6, No. 6, pISSN: 2287-5891, Jun. 30, 2017, 10 pages.

* cited by examiner

| NO. | ITEM | ITEM | TIME | AMOUNT OF CHANGE | SCORE |
|---|---|---|---|---|---|
| 1 | BIO-SIGNAL | A. HEART RATE | WITHIN LAST 5 SECONDS | INCREASED BY EQUAL TO OR MORE THAN 30 BPM | 30 |
| | | | | INCREASED BY RANGE BETWEEN 20 AND 30 BPM | 20 |
| | | | | INCREASED BY RANGE BETWEEN 10 AND 20 BPM | 10 |
| 2 | | B. GSR | WITHIN LAST 5 SECONDS | INCREASED | 15 |
| 3 | | C. BODY TEMPERATURE | WITHIN LAST 5 SECONDS | INCREASED BY EQUAL TO OR MORE THAN 1°C | 10 |
| | | | | INCREASED BY RANGE OF 0.5 AND 1 °C | 5 |
| 4 | | D. VOICE | WITHIN LAST 3 SECONDS | dB INCREASE, SPECIFIC WORD MENTIONED | 10 |
| 5 | | E. FACIAL EXPRESSION | WITHIN LAST 3 SECONDS | SURPRISE, ANGER, ANNOYANCE | 10 |
| 6 | | F. STRESS | WITHIN LAST 5 SECONDS | STRESS LEVEL CHANGE | 5 |
| 7 | VEHICLE SIGNAL | G. WHETHER VEHICLE HAS DEVIATED LINE | WITHIN LAST 1 SECOND | SENSING THAT VEHICLE HAS DEVIATED LINE | 5 |
| 8 | | H. VEHICLE SPEED | WITHIN LAST 1 SECOND | DECREASED BY EQUAL TO OR MORE THAN 30KM/H | 20 |
| | | | | DECREASED BY RANGE BETWEEN 20 AND 30KM/H | 15 |
| | | | | DECREASED BY RANGE BETWEEN 10 AND 20KM/H | 10 |
| 9 | | I. STEERING WHEEL ANGLE | WITHIN LAST 1 SECOND | MANIPULATED BY EQUAL TO OR MORE THAN 30° | 15 |
| | | | | MANIPULATED BY RANGE BETWEEN 20 AND 30° | 10 |
| | | | | MANIPULATED BY RANGE BETWEEN 10 AND 20° | 5 |

DEVICE AND METHOD FOR RECORDING IMAGE FOR VEHICLE

CROSS-REFERENCE TO RELATED APPLICATIONS

This application claims the benefit of Korean Patent Application No. 10-2020-0163220, filed in the Korean Intellectual Property Office on Nov. 27, 2020, which application is hereby incorporated herein by reference.

TECHNICAL FIELD

The present disclosure relates to a device and a method for recording an image for a vehicle.

BACKGROUND

A built-in cam of a vehicle is able to record an image of a region in front of/at the rear of the vehicle during travel or parking, and the recorded image is able to be utilized as a reference or used in a process of finding a cause when an accident occurs.

In a case of an existing built-in cam, the recording may be performed by being distinguished into travel constant recording, travel event (manual) recording, parking constant recording, parking event recording, time lapse recording, and the like.

By the travel constant recording, the image is automatically recorded and stored when the vehicle travels even when a driver does not act separately. However, because there is a limit in a storage capacity, only an image 2 to 3 hours old remains in a memory, and an image recorded before that is deleted as a new travel image is stored.

By a travel event recording function, a recorded image of a total of 20 seconds, 10 seconds before/after a time point at which the accident is suspected, determined using a G sensor of the vehicle, or a time point at which the driver manually pressed a switch of the built-in cam, may be stored in a space where the image is not deleted.

However, when the vehicle is not able to sense an event because the accident has not occurred directly, and the driver fails to press an event recording switch because of being in panic, a necessary portion of the recorded image is not stored in the space where the image is not deleted and the recorded image is able to be deleted by another image.

In addition, with a recent development of a technology of measuring a bio-signal in the vehicle, a bio-signal of the driver such as stress, a state of tension, and the like may be collected using a bezel electrode, a radar sensor, an IR camera, a body temperature sensor, and the like in the vehicle.

Accordingly, there is a need for a technology for determining a specific event by measuring the bio-signal of the driver and storing the recorded image in the space where the image is not deleted.

SUMMARY

The present disclosure relates to a device and a method for recording an image for a vehicle. Particular embodiments relate to a device and a method for storing a recorded vehicle image.

Embodiments of the present disclosure can solve problems occurring in the prior art while advantages achieved by the prior art are maintained intact.

An embodiment of the present disclosure provides a device and a method for recording an image for a vehicle that may determine an image section to be stored in a space where an image is not deleted of a recorded image of a built-in cam using a bio-signal, and prevent deletion of a necessary image.

Another embodiment of the present disclosure provides a device and a method for recording an image for a vehicle that provide high reliability in a process of determining a section requiring image storage using a bio-signal or a vehicle signal even when the vehicle has not sensed an occurrence of an accident through a G sensor.

Another embodiment of the present disclosure provides a device and a method for recording an image for a vehicle that contribute to a convenience of a driver by determining a section requiring image storage using a bio-signal or a vehicle signal by itself even when the driver failed to store the image because of being in panic and not being able to press a switch when the image storage is required.

Another embodiment of the present disclosure provides a device and a method for recording an image for a vehicle that determine a section requiring image storage by itself using a bio-signal or a vehicle signal and store the image in a space where the image is not deleted, thereby utilizing the image for finding a cause of an accident and as a reference.

The technical problems to be solved by embodiments of the present inventive concept are not limited to the aforementioned problems, and any other technical problems not mentioned herein will be clearly understood from the following description by those skilled in the art to which the present disclosure pertains.

According to an embodiment of the present disclosure, a device for recording an image for a vehicle includes an image acquisition device that acquires an image of a region around the vehicle, a sensor device that acquires a bio-signal including at least one of a heart rate, an electrocardiogram, a galvanic skin response (GSR), a body temperature, a voice, a facial expression, and stress of a driver, and a controller that determines some sections to be stored in a non-volatile memory of the acquired image based on the bio-signal, and stores images of said some sections in the non-volatile memory.

In one implementation, the sensor device may acquire a vehicle signal including at least one of whether the vehicle has deviated a line, a vehicle speed, and/or a steering wheel angle, and the controller may determine said some sections to be stored in the non-volatile memory of the acquired image based on at least one of the bio-signal and/or the vehicle signal.

In one implementation, the sensor device may include at least one of an electrocardiogram (ECG) electrode, an electrostatic sensor, a radar, an infra-red (IR) camera, a body temperature meter, a skin temperature (SKT) sensor, a microphone, a GSR sensor, and/or a camera for acquiring the bio-signal.

In one implementation, the sensor device may include at least one of a lane keeping assist system (LKAS), a vehicle speed sensor, a cluster, and a steering angle sensor (SAS) for acquiring the vehicle signal.

In one implementation, the controller may determine an event time point, wherein a final score calculated through an individual score calculated by applying a weight for each of one or more items of the heart rate, the electrocardiogram, the GSR, the body temperature, the voice, and the stress corresponding to items of the bio-signal and whether the vehicle has deviated the line, the vehicle speed, and the steering wheel angle corresponding to items of the vehicle signal exceeds a threshold score at the event time point, and determine said some sections to be stored in the non-volatile memory of the acquired image based on the event time point.

In one implementation, the controller may determine the event time point, wherein the final score exceeds the threshold score and the final score is not calculated only by the individual score of the item corresponding to the vehicle signal at the event time point.

In one implementation, a weight assigned to the heart rate may include the greatest weight among weights assigned to the items of the bio-signal, and a weight assigned to the vehicle speed may include the greatest weight among weights assigned to the items of the vehicle signal.

In one implementation, the controller may calculate the individual score of the item including at least one of the heart rate, the electrocardiogram, the GSR, the body temperature, the voice, the facial expression, the stress, whether the vehicle has deviated the line, the vehicle speed, and/or the steering wheel angle based on a change corresponding to the item within a predetermined time for each item.

In one implementation, the controller may calculate an individual score corresponding to an item of the facial expression when the facial expression is recognized as a facial expression corresponding to a specific emotion.

In one implementation, the controller may calculate an item of the voice when a specific word is recognized through the acquired voice.

In one implementation, the controller may determine sections respectively corresponding to specific times before and after the event time point as some sections to be stored in the non-volatile memory.

According to another embodiment of the present disclosure, a method for recording an image for a vehicle includes acquiring an image of a region around the vehicle, acquiring a bio-signal including at least one of a heart rate, an electrocardiogram, a GSR, a body temperature, a voice, a facial expression, and stress of a driver, and determining some sections to be stored in a non-volatile memory of the acquired image based on the bio-signal, and storing images of said some sections in the non-volatile memory.

In one implementation, the method may further include acquiring a vehicle signal including at least one of whether the vehicle has deviated a line, a vehicle speed, and/or a steering wheel angle, and the determining of said some sections to be stored in the non-volatile memory of the acquired image based on the bio-signal may include determining said some sections to be stored in the non-volatile memory of the acquired image based on at least one of the bio-signal and/or the vehicle signal.

In one implementation, the determining of said some sections to be stored in the non-volatile memory of the acquired image based on at least one of the bio-signal and/or the vehicle signal may include calculating an individual score by assigning a weight for each item of at least one of the heart rate, the electrocardiogram, the GSR, the body temperature, the voice, the facial expression, the stress corresponding to items of the bio-signal, whether the vehicle has deviated the line, the vehicle speed, and/or the steering wheel angle corresponding to items of the vehicle signal, determining an event time point, wherein a final score calculated by the individual score exceeds a threshold score, and determining some sections to be stored in the non-volatile memory of the acquired image based on the event time point.

In one implementation, the determining of the event time point may include determining the event time point, wherein the final score exceeds the threshold score and the calculated final score is not calculated only by the individual score of the item corresponding to the vehicle signal at the event time point.

In one implementation, a weight assigned to the heart rate may include the greatest weight among weights assigned to the items of the bio-signal, and a weight assigned to the vehicle speed may include the greatest weight among weights assigned to the items of the vehicle signal.

In one implementation, the calculating of the individual score may include calculating the individual score of the item including at least one of the heart rate, the electrocardiogram, the GSR, the body temperature, the voice, the facial expression, the stress, whether the vehicle has deviated the line, the vehicle speed, and/or the steering wheel angle based on a change corresponding to the item within a predetermined time for each item.

In one implementation, the calculating of the individual score may include calculating an individual score corresponding to an item of the facial expression when the facial expression is recognized as a facial expression corresponding to a specific emotion.

In one implementation, the calculating of the individual score may include calculating the individual score corresponding to an item of the voice when a specific word is recognized through the acquired voice.

In one implementation, the determining of said some sections to be stored in the non-volatile memory of the acquired image based on the event time point may include determining sections respectively corresponding to specific times before and after the event time point as said some sections to be stored in the non-volatile memory.

BRIEF DESCRIPTION OF THE DRAWINGS

The above and other objects, features and advantages of embodiments of the present disclosure will be more apparent from the following detailed description taken in conjunction with the accompanying drawings, in which.

DETAILED DESCRIPTION OF ILLUSTRATIVE EMBODIMENTS

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiments of the present disclosure, a detailed description of the related known configuration or function will be omitted when it is determined that it interferes with the understanding of the embodiments of the present disclosure.

In describing the components of the embodiments according to the present disclosure, terms such as first, second, A, B, (a), (b), and the like may be used. These terms are merely intended to distinguish the components from other components, and the terms do not limit the nature, order or sequence of the components. Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, embodiments of the present disclosure will be described in detail with reference to FIGS. 1 to 7.

Figure 1:
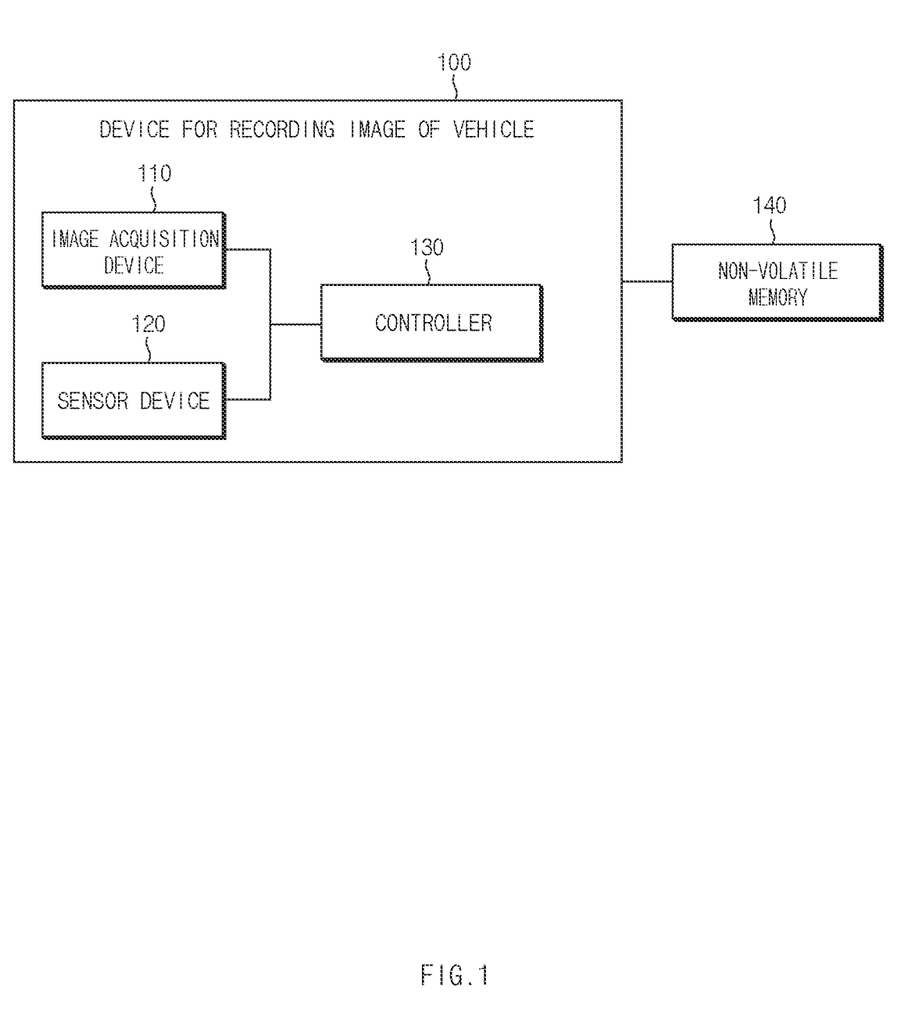
FIG. 1 is a block diagram illustrating a device for recording an image for a vehicle according to an embodiment of the present disclosure.

FIG. 1 is a block diagram illustrating a device for recording an image for a vehicle according to an embodiment of the present disclosure.

Referring to FIG. 1, a device 100 for recording an image of a vehicle may be implemented including an image acquisition device 110, a sensor device 120, and a controller 130.

The device 100 for recording the image of the vehicle may be formed integrally with the vehicle, or may be implemented in a form of being installed in/attached to the vehicle as a separate component from the vehicle. A portion of the device 100 may be implemented integrally with the vehicle, and the remaining portion thereof may be implemented in the form of being installed in/attached to the vehicle as the separate component from the vehicle.

The image acquisition device 110 may acquire an image of a region around the vehicle.

As an example, the image acquisition device 110 may capture the image of the region around the vehicle by including one or more cameras mounted on front/rear and left/right surfaces of the vehicle.

As an example, the image acquisition device 110 may acquire an image of the region around the vehicle of a composition capable of identifying an accident situation when an accident occurs.

As an example, the image acquisition device 110 may include a black box for the vehicle and an advanced driver assistance system (ADAS) sensor.

The sensor device 120 may acquire a bio-signal including at least one of a heart rate, an electrocardiogram, a galvanic skin response (GSR), a body temperature, a voice, a facial expression, and/or stress of a driver.

In addition, the sensor device 120 may acquire a vehicle signal including at least one of whether the vehicle has deviated a line, a vehicle speed, and/or a steering wheel angle.

As an example, the sensor device 120 may include at least one of an electrocardiogram (ECG) electrode, an electrostatic sensor, a radar, an infra-red (IR) camera, a body temperature meter, a skin temperature (SKT) sensor, a microphone, a GSR sensor, and/or a camera for acquiring the bio-signal.

As an example, the sensor device 120 may include at least one of a lane keeping assist system (LKAS), a vehicle speed sensor, a cluster, and/or a steering angle sensor (SAS) for acquiring the vehicle signal.

The controller 130 may perform overall control such that each component is able to normally perform a function thereof. Such controller 130 may be implemented in a form of hardware, software, or a combination of the hardware and the software. Preferably, the controller 130 may be implemented as a microprocessor, but may not be limited thereto. In addition, the controller 130 may perform various data processing, calculations, and the like to be described later.

As an example, the controller 130 may receive the bio-signal and the vehicle signal acquired from the sensor device 120 and perform an operation using the received bio-signal and vehicle signal.

As an example, the controller 130 may control storage or deletion of the image by receiving information on the image acquired from the image acquisition device 100.

As an example, the controller 130 may be connected to a non-volatile memory 140 to store the image acquired from the image acquisition device 110 in the non-volatile memory 140.

As an example, the controller 130 may determine some sections stored in the non-volatile memory of an image acquired based on the bio-signal, and store an image of some sections in the non-volatile memory 140.

As an example, the controller 130 may determine some sections stored in the non-volatile memory of an image acquired based on at least one of the bio-signal and/or the vehicle signal, and store an image of some sections in the non-volatile memory 140.

The non-volatile memory 140 may be connected to the device 100 for recording the image for the vehicle to exchange information.

The non-volatile memory 140 may store image data, and the stored image data may not be erased even when the non-volatile memory 140 is switched off.

The non-volatile memory 140 may be disposed outside the device 100 for recording the image for the vehicle, but may be included in the device 100 for recording the image for the vehicle.

Figure 2:
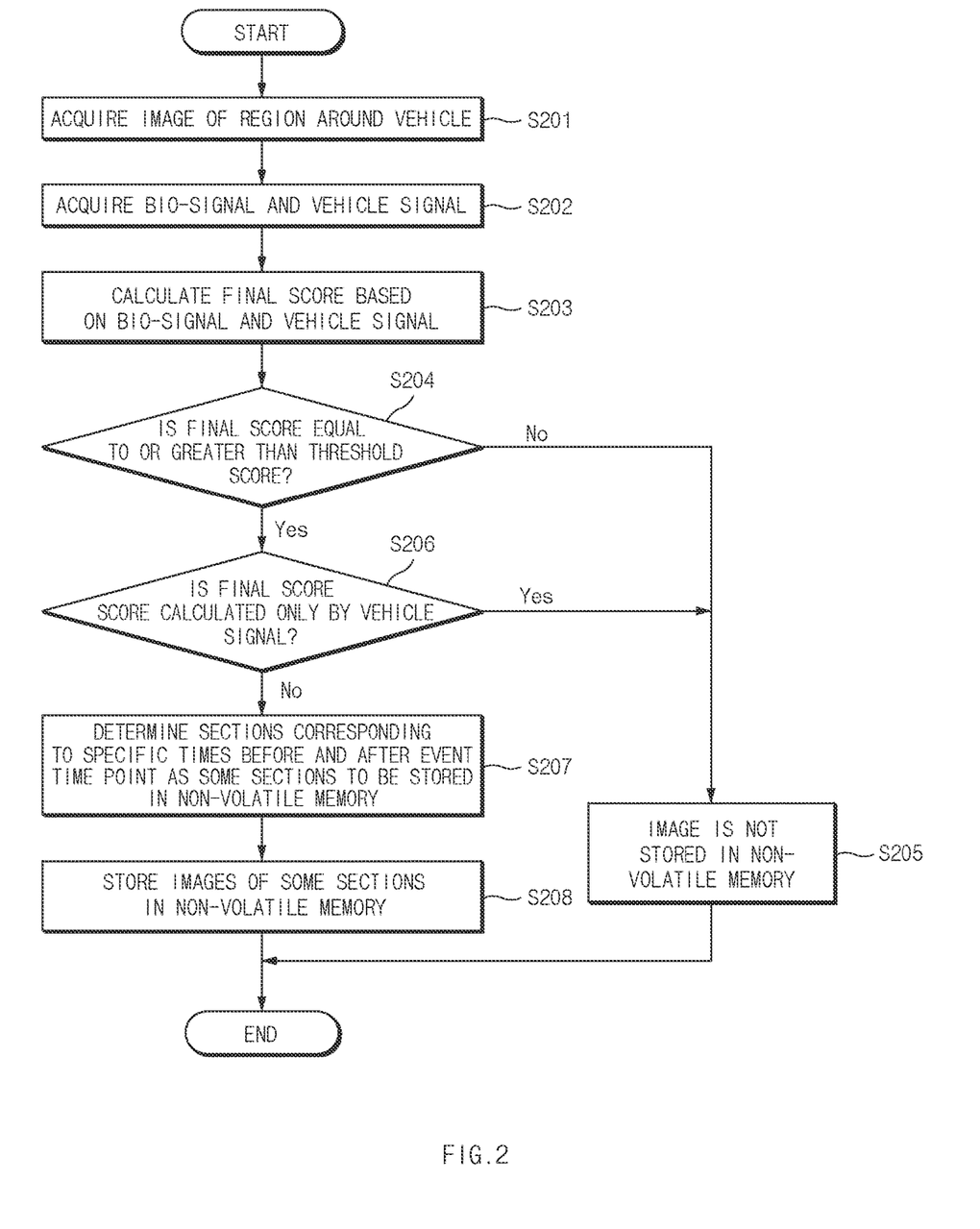
FIG. 2 is a flowchart illustrating a method for recording an image for a vehicle according to an embodiment of the present disclosure.

FIG. 2 is a flowchart illustrating a method for recording an image for a vehicle according to an embodiment of the present disclosure.

The device 100 for recording the image for the vehicle may acquire the image of the region around the vehicle (S201).

As an example, the device 100 for recording the image for the vehicle may acquire images of regions ahead/at the rear and on a left/right side of the vehicle.

The device 100 for recording the image for the vehicle may acquire the image of the region around the vehicle and then acquire the bio-signal and the vehicle signal (S202).

As an example, the device 100 for recording the image for the vehicle may acquire the bio-signal including at least one of the heart rate, the electrocardiogram, the galvanic skin response (GSR), the body temperature, the voice, the facial expression, and/or the stress of the driver, and the vehicle signal including at least one of whether the vehicle has deviated the line, the vehicle speed, and/or the steering wheel angle through the sensor device 120.

After acquiring the bio-signal and the vehicle signal, the device 100 for recording the image for the vehicle may calculate a final score based on the bio-signal and the vehicle signal (S203).

As an example, the device 100 for recording the image for the vehicle may calculate an individual score by applying a weight for each item of at least one of the heart rate, the electrocardiogram, the GSR, the body temperature, the voice, the facial expression, and the stress corresponding to items of the bio-signal, and whether the vehicle has deviated the line, the vehicle speed, and/or the steering wheel angle corresponding to items of the vehicle signal.

As an example, the device 100 for recording the image for the vehicle may calculate the final score through the calculated individual score.

As an example, the device 100 for recording the image for the vehicle may calculate the final score in a scheme of summing the individual scores or a scheme of calculating a weight sum of the individual scores.

An example of obtaining the individual scores and the final score will be described in detail in FIG. 3.

After calculating the final score based on the bio-signal and the vehicle signal, the device 100 for recording the image for the vehicle may determine whether the final score is equal to or greater than a threshold score (S204).

As an example, the threshold score may be a score value determined in advance by an experiment and stored in a memory, and may be a score that may be updated to a new value.

As an example, the device 100 for recording the image for the vehicle may determine whether the final score calculated in real time is equal to or greater than the threshold score to determine an event time point at which the final score becomes equal to or greater than the threshold score.

In this process, the device 100 for recording the image for the vehicle may be designed to determine whether the final score exceeds the threshold score according to an embodiment without being limited to the word 'equal to or greater than'.

The device 100 for recording the image for the vehicle may not store the image in the non-volatile memory when the final score is not equal to or greater than the threshold score (S205).

As an example, the device 100 for recording the image for the vehicle may not store the image in the non-volatile memory, but may store the image in a volatile memory. When a capacity of the volatile memory is insufficient due to an image being recorded, the device 100 may delete an image of the oldest section stored in the volatile memory and store a new image in the volatile memory.

The device 100 for recording the image for the vehicle may determine whether the final score is a score calculated only by the vehicle signal when the final score is equal to or greater than the threshold score (S206).

As an example, when the final score is calculated by summing the individual scores respectively corresponding to the items for the bio-signal and the vehicle signal, the device 100 for recording the image for the vehicle may determine whether the final score is equal to or greater than the threshold score by being summed only by the scores corresponding to the vehicle signal as the individual scores corresponding to the bio-signal are not calculated or 0 is calculated.

The device 100 for recording the image for the vehicle may not store the image in the non-volatile memory when the final score is a score calculated only by the vehicle signal (S205).

As an example, when the final score is calculated by summing the individual scores respectively corresponding to the items for the bio-signal and the vehicle signal, the device 100 for recording the image for the vehicle may prioritize the item of the bio-signal over the item of the vehicle signal. When the individual scores corresponding to the items of the bio-signal are not calculated or o is calculated, and when the final score obtained by summing only the scores corresponding to the vehicle signal is equal to or greater than the threshold score, the device 100 may not store the image in the non-volatile memory.

When the final score is not the score calculated only by the vehicle signal, the device 100 for recording the image for the vehicle may store sections respectively corresponding to specific times before and after the event time point in the non-volatile memory (S207 and S208).

As an example, the device 100 for recording the image for the vehicle may determine a time point at which the final score becomes equal to or greater than the threshold score as the event time point, and store the sections respectively corresponding to the specific times before and after the event time point in the non-volatile memory.

As an example, the device 100 for recording the image for the vehicle may store the sections respectively corresponding to the specific times before and after the event time point in the non-volatile memory 140 through a value of the specific time that has already been determined through an experiment and stored in the memory.

As an example, the device 100 for recording the image for the vehicle may move or copy sections respectively corresponding to the specific times before and after the event time point of the image stored in the volatile memory to the non-volatile memory 140.

Figure 3:
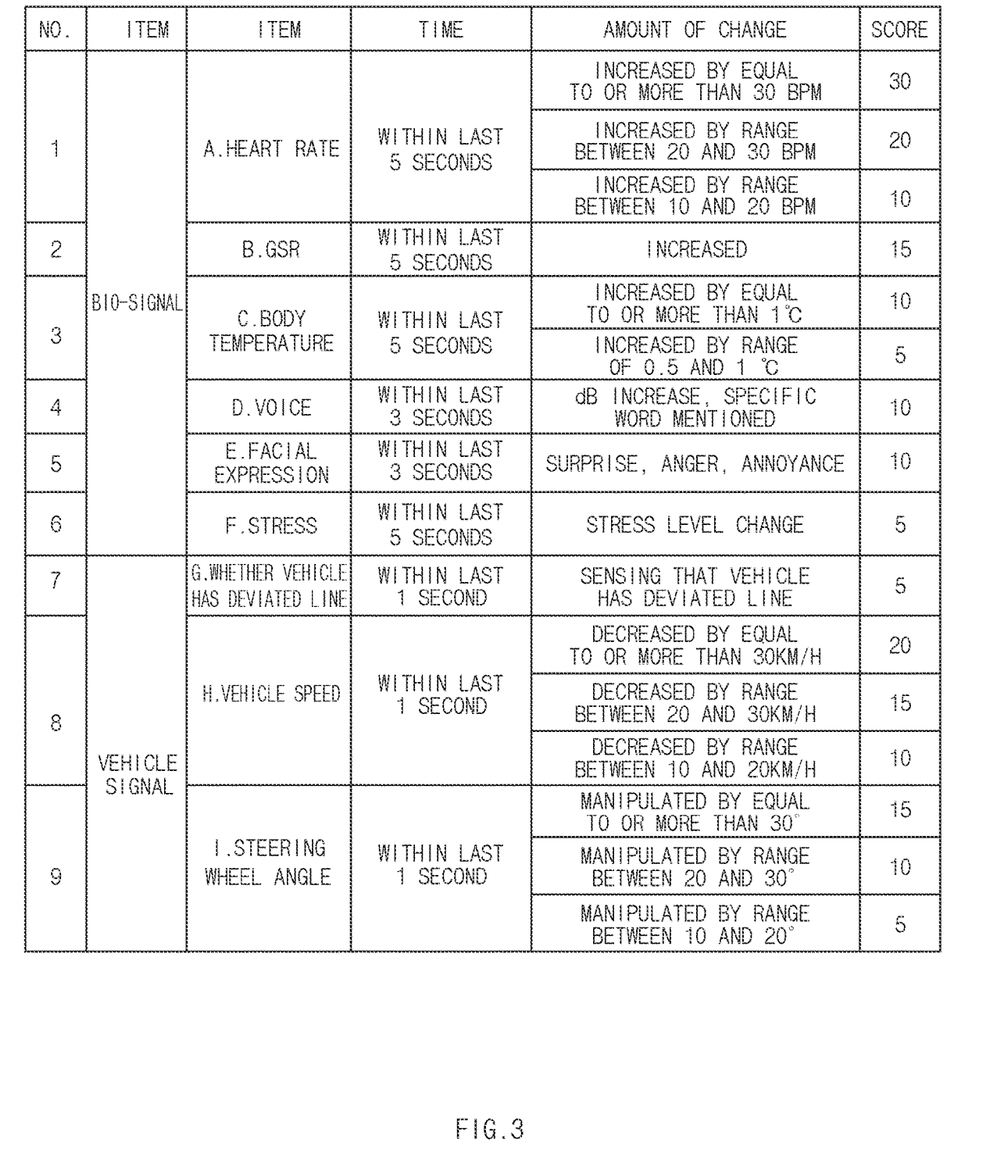
FIG. 3 is a diagram illustrating a process of calculating an individual score based on each item by a device for recording an image for a vehicle according to an embodiment of the present disclosure in a table.

FIG. 3 is a diagram illustrating a process of calculating an individual score based on each item by a device for recording an image for a vehicle according to an embodiment of the present disclosure in a table.

According to the table of FIG. 3, the items of the bio-signal may include the heart rate, the GSR, the body temperature, the voice, the facial expression, and the stress.

Although not shown, the items of the bio-signal may include the electrocardiogram.

The items of the vehicle signal may include whether the vehicle has deviated the line, the vehicle speed, and the steering wheel angle.

As an example, the device 100 for recording the image for the vehicle may calculate the individual score of the item including at least one of the heart rate, the electrocardiogram, the GSR, the body temperature, the voice, the facial expression, the stress, whether the vehicle has deviated the line, the vehicle speed, and/or the steering wheel angle based on a change corresponding to the item within a predetermined time for each item.

As an example, the device 100 for recording the image for the vehicle may calculate an individual score based on an amount of change within the last 5 seconds with respect to the heart rate among the items of the bio-signal.

As an example, the device 100 for recording the image for the vehicle may calculate the individual score for the heart rate as 30 points when the heart rate has increased by equal to or more than 30 bpm within the last 5 seconds.

As an example, the device 100 for recording the image for the vehicle may calculate the individual score for the heart rate as 20 points when the heart rate is increased by a range between 20 and 30 bpm within the last 5 seconds.

As an example, the device 100 for recording the image for the vehicle may calculate the individual score for the heart rate as 10 points when the heart rate is increased by a range between 10 and 20 bpm within the last 5 seconds.

As an example, the device 100 for recording the image for the vehicle may calculate an individual score based on an amount of change within the last 5 seconds with respect to the GSR among the items of the bio-signal.

As an example, the device 100 for recording the image for the vehicle may calculate the individual score for the GSR as 15 points when there is a change in the GSR of increasing within the last 5 seconds.

As an example, the device 100 for recording the image for the vehicle may calculate an individual score based on an amount of change within the last 5 seconds with respect to the body temperature among the items of the bio-signal.

As an example, the device 100 for recording the image for the vehicle may calculate the individual score for the body temperature as 10 points when the body temperature is increased by equal to or more than 1° C. within 5 seconds.

As an example, the device 100 for recording the image for the vehicle may calculate the individual score for the body temperature as 5 points when the body temperature is increased by a range of 0.5 and 1° C. within the last 5 seconds.

As an example, the device 100 for recording the image for the vehicle may calculate an individual score based on an amount of change within the last 3 seconds with respect to the voice among the items of the bio-signal.

As an example, the device 100 for recording the image for the vehicle may calculate the individual score for the voice as 10 points when a decibel dB of a volume of the voice is increased within the last 3 seconds.

As an example, the device 100 for recording the image for the vehicle may calculate the individual score for the voice as 10 points when it is determined that a specific word is mentioned through the voice within the last 3 seconds.

As an example, the device 100 for recording the image for the vehicle may determine a voice tone and pre-set words that may represent surprise, annoyance, excitement, anger, and the like such as "Oh my!", "What a surprise!", other swear words, and the like through a technology of recognizing a voice of a user, processing a natural language, and recognizing the word, and assign a score when the corresponding word is recognized.

As an example, the device 100 for recording the image for the vehicle may calculate an individual score based on a change within the last 3 seconds with respect to the facial expression among the items of the bio-signal.

As an example, the device 100 for recording the image for the vehicle may calculate the individual score for the facial expression as 10 points when a facial expression within the last 3 seconds is determined to be a facial expression corresponding to a specific emotion such as surprise, anger, annoyance, and the like.

A process of recognizing the facial expression will be described in detail in FIG. 6.

As an example, the device 100 for recording the image for the vehicle may calculate an individual score based on a change within the last 5 seconds with respect to the stress among the items of the bio-signal.

As an example, the device 100 for recording the image for the vehicle may calculate the individual score for the stress as 5 points when there is a change in a stress level within the last 5 seconds.

As an example, the device 100 for recording the image for the vehicle may calculate an individual score based on a change within the last 1 second with respect to whether the vehicle has deviated the line among the items of the vehicle signal.

As an example, the device 100 for recording the image for the vehicle may calculate the individual score for whether the vehicle has deviated the line as 5 points when the line deviation is sensed within the last 1 second.

As an example, the device 100 for recording the image for the vehicle may calculate an individual score based on an amount of change within the last 1 second with respect to the vehicle speed among the items of the vehicle signal.

As an example, the device 100 for recording the image for the vehicle may calculate the individual score for the vehicle speed as 20 points when the vehicle speed decreases by equal to or more than 30 km/h within the last 1 second.

As an example, the device 100 for recording the image for the vehicle may calculate the individual score for the vehicle speed as 15 points when the vehicle speed decreases by a range between 20 and 30 km/h within the last 1 second.

As an example, the device 100 for recording the image for the vehicle may calculate the individual score for the vehicle speed as 10 points when the vehicle speed decreases by a range between 10 and 20 km/h within the last 1 second.

As an example, the device 100 for recording the image for the vehicle may calculate an individual score based on an amount of change within the last 1 second with respect to the steering wheel angle among the items of the vehicle signal.

As an example, the device 100 for recording the image for the vehicle may calculate the individual score for the steering wheel angle as 15 points when the steering wheel angle is decreased by equal to or more than 30° within the last 1 second.

As an example, the device 100 for recording the image for the vehicle may calculate the individual score for the steering wheel angle as 10 points when the steering wheel angle is decreased by a range between 20 and 30° within the last 1 second.

As an example, the device 100 or recording the image for the vehicle may calculate the individual score for the steering wheel angle as 5 points when the steering wheel angle is decreased by a range between 10 and 20° within the last 1 second.

Although not shown, the device 100 for recording the image for the vehicle may calculate an individual score based on a change within a recent specific time with respect to the electrocardiogram among the items of the bio-signal.

As an example, the device 100 for recording the image for the vehicle may calculate the individual score for the electrocardiogram as 20 points when there is a change in the electrocardiogram within the last 5 seconds.

The device 100 for recording the image for the vehicle may calculate the final score by summing all the calculated individual scores.

As an example, the device 100 for recording the image for the vehicle may determine an event time point at which the calculated final score exceeds the threshold score set as 20 points.

As an example, even when the calculated final score exceeds the threshold score, the device 100 for recording the image for the vehicle may not determine a time point at which the final score exceeds the threshold score as the event time point by prioritizing the bio-signal when the final score is obtained by summing only by the items of the vehicle signal.

For example, when the individual score corresponding to the heart rate is 10 points, the individual score corresponding to the facial expression is 5 points, and the score corresponding to the vehicle speed is 10 points to be a total of 25 points, the device 100 for recording the image for the vehicle may determine the time point at which the final score exceeds the threshold score as the event time point. When the score corresponding to whether the vehicle has deviated the line is 5 points, the score corresponding to the vehicle speed is 15 points, and the score corresponding to the steering wheel angle is 5 points, the device 100 for recording the image for the vehicle may not determine the time point at which the final score exceeds the threshold score as the event time point.

Weight values calculated at specific times and specific conditions of the individual scores and the threshold score illustrated in the description of FIG. 3 are exemplary numerical values, and are not limited to the specified values. Actually, the weight values and the threshold score may be set to other values determined through an experiment, or may be designed to be updated later.

In addition, a condition for determining the event time point is not limited to the word 'exceeding' in the condition of exceeding the threshold score, and also includes a condition of exceeding or being equal to or greater than the threshold score according to an embodiment.

A criterion for setting the condition for assigning the weights and the scores assigned to the items of the bio-signal and the vehicle signal will be described in detail.

It is the heart rate and the GSR by an autonomic nervous system that a reaction may appear most quickly by five senses of a living body. That is, the GSR and the heart rate respectively corresponding to a skin conductance and a peripheral vascular response may sensitively express a driving situation, while the body temperature corresponding to a skin temperature may partially reflect the driving situation.

However, for the GSR sensor to sense the change, sweat must come out of a hand and the driver must grip the steering wheel or the like on which a contact-type sensor is located. On the other hand, the heart rate shows an immediate response resulted from stimulation of the five senses of the human body, and is able to be measured without being contacted through the radar/PPG/IR sensor and the like.

In consideration of such points, a weight of the score of the heart rate item may be relatively great compared to weights of other items.

As an example, a weight assigned to the heart rate may include the largest weight among weights assigned to the items of the bio-signal.

In addition, because the voice and the facial expression may change by reasons (phone call, conversation with a passenger in a passenger seat, and the like) other than an emergency situation, weights for the scores of the voice and the facial expression may be relatively small compared to weights of other items such that the individual scores of the voice and the facial expression may be assigned for assisting scores of other items.

In addition, because the stress is less responsive than the heart rate and there may be a driver having chronic stress, a condition may be set such that the score for the stress may be assigned when the stress level changes. In addition, a weight for the score for the stress may be set to the lowest among weights of the items of the bio-signal.

When the vehicle speed is rapidly reduced, it may be expected that there will be the emergency situation ahead of the vehicle, so that a weight for the score of the vehicle speed may be set relatively high compared to weights of other items.

Manipulation of the steering wheel may exist in a situation of a lane change, a left turn, or a right turn intended by the driver, and thus a weight for the score of the steering wheel angle may be set relatively low compared to weights of other items.

Figure 4:
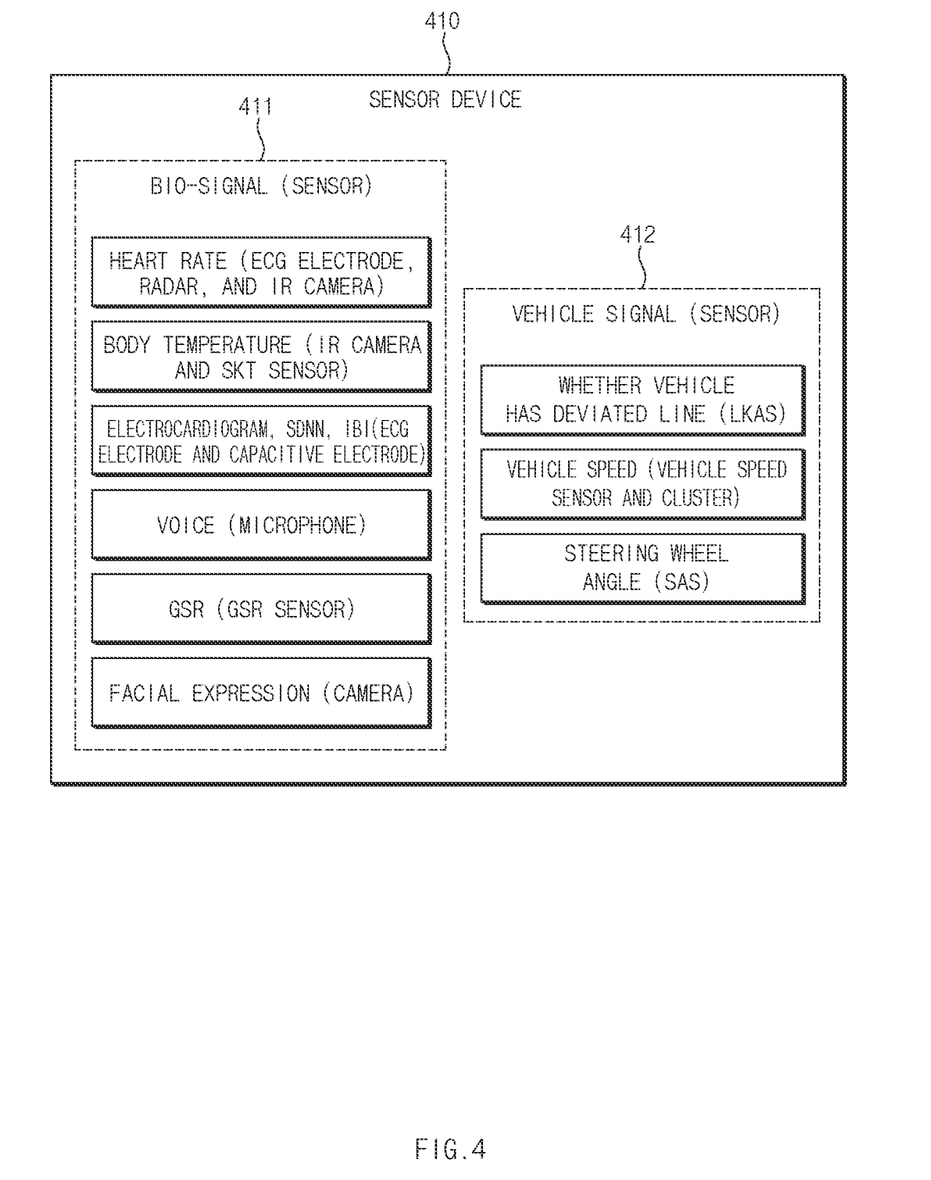
FIG. 4 is a diagram illustrating items of a bio-signal and a vehicle signal acquired by a sensor device of a device for recording an image for a vehicle according to an embodiment of the present disclosure.

FIG. 4 is a diagram illustrating items of a bio-signal and a vehicle signal acquired by a sensor device of a device for recording an image for a vehicle according to an embodiment of the present disclosure.

According to FIG. 4, a sensor device 410 may acquire a bio-signal 411 including the heart rate, the electrocardiogram, the body temperature, the GSR, the voice, and the facial expression.

Although not shown, the bio-signal 411 may include the stress.

As an example, the sensor device 410 may include at least one of the ECG electrode, the radar, and/or the IR camera, and acquire the heart rate of the driver through at least one of the ECG electrode, the radar, and/or the IR camera.

As an example, the ECG electrode is disposed on the steering wheel to acquire the heart rate of the driver.

As an example, the sensor device 410 may include at least one of the IR camera and/or the SKT sensor, and acquire the body temperature of the driver through at least one of the IR camera and/or the SKT sensor.

As an example, the sensor device 410 may include at least one of the ECG electrode and/or the electrostatic sensor, and may acquire at least one of the electrocardiogram, a standard deviation of the NN interval (SDNN) and/or an inter beat interval (IBI) of the driver through at least one of the ECG electrode and/or the electrostatic sensor.

As an example, the ECG electrode may be disposed on the steering wheel to acquire at least one of the electrocardiogram, the SDNN, and/or the IBI of the driver.

As an example, the sensor device 410 may include the microphone, and may acquire the voice of the driver through the microphone.

As an example, the sensor device 410 may include the GSR sensor, and acquire the GSR of the driver through the GSR sensor.

As an example, the GSR sensor may be disposed on the steering wheel to acquire the GSR of the driver.

As an example, the sensor device 410 may include the camera, and acquire the facial expression of the driver through the camera.

Although not shown, as an example, the sensor device 410 may include a wearable sensor, and acquire the stress level of the driver through the wearable sensor.

The sensor device 410 may acquire a vehicle signal 412 including whether the vehicle has deviated the line, the vehicle speed, and the steering wheel angle.

As an example, the sensor device 410 may include the LKAS, and acquire whether the vehicle has deviated the line through the LKAS.

As an example, the sensor device 410 may include at least one of the vehicle speed sensor and/or the cluster, and acquire the vehicle speed through at least one of the vehicle speed sensor and/or the cluster.

As an example, the sensor device 410 may include the SAS, and acquire the steering wheel angle through the SAS.

Figure 5:
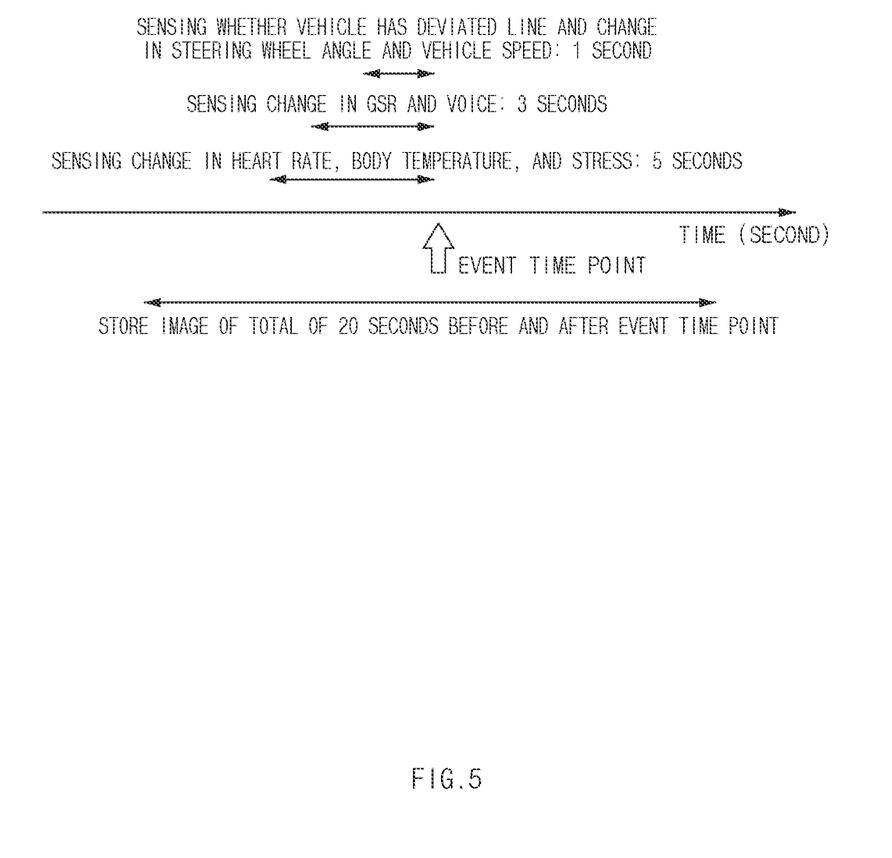
FIG. 5 is a diagram illustrating a process of determining an event time point by a device for recording an image for a vehicle according to an embodiment of the present disclosure.

FIG. 5 is a diagram illustrating a process of determining an event time point by a device for recording an image for a vehicle according to an embodiment of the present disclosure.

The device 100 for recording the image for the vehicle may determine the event time point at which the calculated final score exceeds the threshold score, and determine the sections corresponding to the specific times before and after the event time point as some sections stored in the non-volatile memory.

The device 100 for recording the image for the vehicle may calculate the final score in real time.

Referring to FIG. 5, the device 100 for recording the image for the vehicle may detect whether the vehicle has deviated the line, and the changes in the vehicle speed and the steering wheel angle within the past 1 second based on a current time point.

As an example, the device 100 for recording the image for the vehicle may detect the changes in the GSR and the voice within the past 3 seconds based on the current time point.

As an example, the device 100 for recording the image for the vehicle may detect the changes in the heart rate, the body temperature, and the stress within the past 5 seconds based on the current time point.

The device 100 for recording the image for the vehicle may calculate the final score by summing the individual scores calculated by the changes in whether the vehicle has deviated the line, the vehicle speed, the steering wheel angle, the GSR, the voice, the heart rate, the body temperature, and the stress, and determine the time point at which the final score exceeds the threshold score as the event time point.

As an example, the device 100 for recording the image for the vehicle may store an image of a total of 20 seconds of sections of 10 seconds before and after the event time point in the non-volatile memory.

Figure 6:
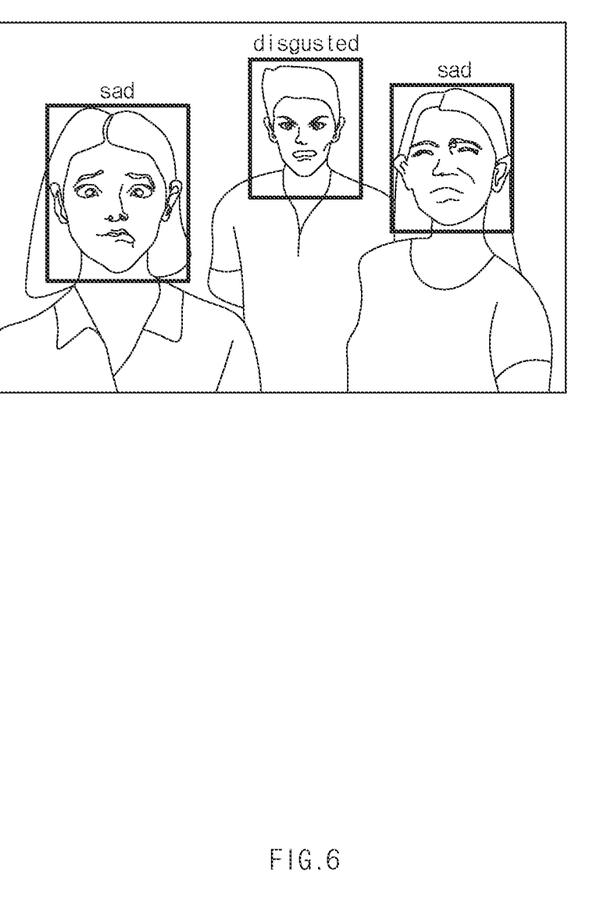
FIG. 6 is a diagram illustrating a process of recognizing a facial expression by a device for recording an image for a vehicle according to an embodiment of the present disclosure.

FIG. 6 is a diagram illustrating a process of recognizing a facial expression by a device for recording an image for a vehicle according to an embodiment of the present disclosure.

The device 100 for recording the image for the vehicle may recognize the facial expression of the driver through a technology of recognizing the facial expression and determining the emotion.

As an example, the technology of recognizing the facial expression and determining the emotion may be implemented through machine learning.

As an example, the device 100 for recording the image for the vehicle may acquire an image of a face of the driver through the camera to sense the facial expression of the driver.

As an example, the device 100 for recording the image for the vehicle may recognize which portion is a face portion in the acquired image.

In addition, the device 100 for recording the image for the vehicle may determine eyebrows, corners of a mouth, frown lines, and the like in the portion recognized as the face in the acquired image to recognize the facial expression of the user based on a movement of the eyebrows, whether the corners of the mouth are lowered, and whether the frown lines are generated as the driver frowns.

Referring to FIG. 6, the device 100 for recording the image for the vehicle may recognize the facial expression such as sad, disgusted, and the like.

As an example, the device 100 for recording the image for the vehicle may calculate the individual score corresponding to the facial expression when a facial expression recognized within a predetermined time is determined as a specific facial expression such as surprise, anger, annoyance, excitement, and the like.

Figure 7:
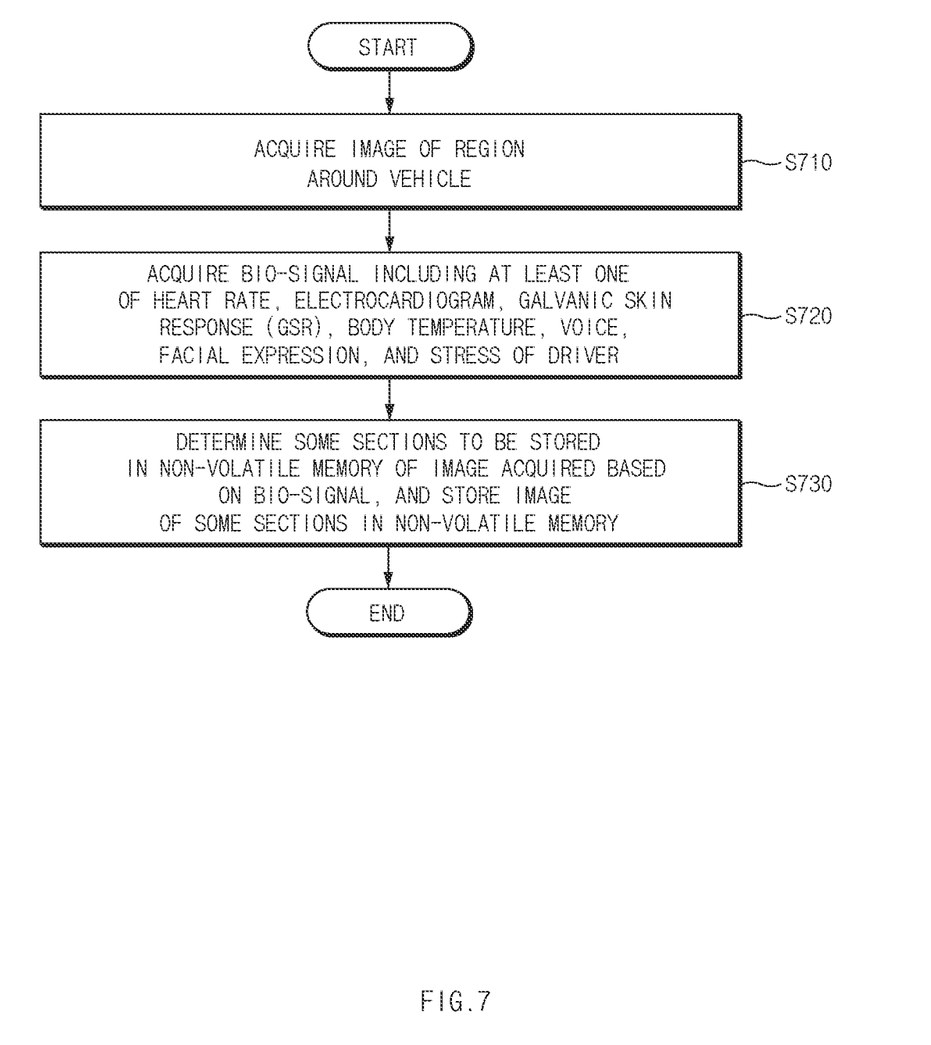
FIG. 7 is a flowchart illustrating a method for recording an image for a vehicle according to another embodiment of the present disclosure.

FIG. 7 is a flowchart illustrating a method for recording an image for a vehicle according to another embodiment of the present disclosure.

Referring to FIG. 7, a method for recording an image for a vehicle may include acquiring the image of the region around the vehicle (S710), acquiring the bio-signal including at least one of the heart rate, the electrocardiogram, the galvanic skin response (GSR), the body temperature, the voice, the facial expression, and the stress of the driver (S720), and determining some sections to be stored in the non-volatile memory of the image acquired based on the bio-signal, and storing the image of some sections in the non-volatile memory (S730).

The acquiring of the image of the region around the vehicle (S710) may be performed through the image acquisition device 110.

The acquiring of the bio-signal including at least one of the heart rate, the electrocardiogram, the galvanic skin response (GSR), the body temperature, the voice, the facial expression, and the stress of the driver (S720) may be performed through at least one of the ECG electrode, the electrostatic sensor, the radar, the IR camera, the body temperature meter, the SKT sensor, the microphone, the GSR sensor, and/or the camera.

The determining of some sections to be stored in the non-volatile memory of the image acquired based on the bio-signal, and the storing of the image of some sections in the non-volatile memory (S730) may include calculating the individual score by applying the weight for each of one or more items of the heart rate, the electrocardiogram, the GSR, the body temperature, the voice, the facial expression, and the stress corresponding to the items of the bio-signal, calculating the final score through the calculated individual scores, determining the event time point at which the calculated final score exceeds the threshold score, and determining the sections respectively corresponding to the specific times before and after the event time point as some sections stored in the non-volatile memory.

The description above is merely illustrative of the technical idea of the present disclosure, and various modifications and changes may be made by those skilled in the art without departing from the essential characteristics of the present disclosure.

Therefore, the embodiments disclosed in the present disclosure are not intended to limit the technical idea of the present disclosure but to illustrate the present disclosure, and the scope of the technical idea of the present disclosure is not limited by the embodiments. The scope of the present disclosure should be construed as being covered by the scope of the appended claims, and all technical ideas falling within the scope of the claims should be construed as being included in the scope of the present disclosure.

Effects of the device and the method for recording the image for the vehicle according to embodiments of the present disclosure will be described as follows.

According to at least one of the embodiments of the present disclosure, the device and the method for recording the image for the vehicle that may determine the image section to be stored in the space where the image is not deleted of the recorded image of the built-in cam using the bio-signal, and prevent the deletion of the necessary image may be provided.

Further, according to at least one of the embodiments of the present disclosure, the device and the method for recording the image for the vehicle that provide the high reliability in the process of determining the section requiring the image storage using the bio-signal or the vehicle signal even when the vehicle has not sensed the occurrence of the accident through the G sensor may be provided.

Further, according to at least one of the embodiments of the present disclosure, the device and the method for recording the image for the vehicle that contribute to the convenience of the driver by determining the section requiring the image storage using the bio-signal or the vehicle signal by itself even when the driver failed to store the image because of being in panic and not being able to press the switch when the image storage is required may be provided.

Further, according to at least one of the embodiments of the present disclosure, the device and the method for recording the image for the vehicle that determine the section requiring the image storage by itself using the bio-signal or the vehicle signal and store the image in the space where the image is not deleted and allow the image to be utilized for finding the cause of the accident and as the reference may be provided.

In addition, various effects that are directly or indirectly identified through the present document may be provided.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A device for recording an image for a vehicle, the device comprising:
    a memory storing program instructions; and
    a processor configured to execute the program instructions, the program instructions, when executed by the processor, cause the processor to:
    receive an image of a region around the vehicle;
    receive a bio-signal of a driver, the bio-signal comprising a signal carrying information selected from the group consisting of a heart rate, an electrocardiogram, a galvanic skin response (GSR), a body temperature, a voice, a facial expression, and a stress level and combinations thereof;
    determine sections of the received image to be stored in a non-volatile memory based on the bio-signal;
    store the sections of the received image in the non-volatile memory;
    determine an event time point, wherein a final score calculated through an individual score calculated by applying a weight for each of one or more items of the heart rate, the electrocardiogram, the GSR, the body temperature, the voice, the stress level corresponding to items of the bio-signal and whether the vehicle has deviated a line, a vehicle speed, and a steering wheel angle corresponding to items of a vehicle signal, exceeds a threshold score at the event time point; and
    determine the sections of the received image to be stored in the non-volatile memory based on the event time point.

2. The device of claim 1, wherein the vehicle signal comprises a signal carrying information selected from the group consisting of whether the vehicle has deviated the line, the vehicle speed, or the steering wheel angle; and
    wherein the program instructions further cause the processor to determine the sections of the received image to be stored in the non- volatile memory based on the bio-signal or the vehicle signal.

3. The device of claim 2, further comprising a sensor device configured to acquire the bio-signal of the driver, wherein the sensor device comprises a lane keeping assist system (LKAS), a vehicle speed sensor, a cluster, or a steering angle sensor (SAS).

4. The device of claim 1, wherein the program instructions further cause the processor to determine the event time point, wherein the final score exceeds the threshold score and the final score is not calculated only by the individual score of the item corresponding to the vehicle signal at the event time point.

5. The device of claim 1, wherein:
    the weight assigned to the heart rate is a greatest weight among weights assigned to the items of the bio-signal; and
    a weight assigned to the vehicle speed is a greatest weight among weights assigned to the items of the vehicle signal.

6. The device of claim 1, wherein the program instructions further cause the processor to calculate the individual score of the item including the heart rate, the electrocardiogram, the GSR, the body temperature, the voice, the facial expression, the stress level, whether the vehicle has deviated the line, the vehicle speed, or the steering wheel angle based on a change corresponding to the item within a predetermined time for each item.

7. The device of claim 1, wherein the program instructions further cause the processor to calculate the individual score corresponding to an item of the facial expression when the facial expression is recognized as corresponding to a specific emotion.

8. The device of claim 1, wherein the program instructions further cause the processor to calculate the individual score corresponding to the voice when a specific word is recognized.

9. The device of claim 1, wherein the program instructions further cause the processor to determine sections respectively corresponding to specific times before and after the event time point as the sections to be stored in the non-volatile memory.

10. The device of claim 1, further comprising:
    an image acquisition device coupled configured to acquire the image of the region around the vehicle and provide the image to the processor; and
    a sensor device configured to acquire the bio-signal of the driver and provide the bio- signal to the processor.

11. The device of claim 10, wherein the sensor device comprises an electrocardiogram (ECG) electrode, an electrostatic sensor, a radar, an infra-red (IR) camera, a body temperature meter, a skin temperature (SKT) sensor, a microphone, a GSR sensor, or a camera.

12. A method for recording an image for a vehicle, the method comprising:
    acquiring an image of a region around the vehicle;
    acquiring a bio-signal comprising a signal carrying information selected from the group consisting of a heart rate, an electrocardiogram, a GSR, a body temperature, a voice, a facial expression, and a stress level of a driver and combinations thereof; and
    determining sections of the acquired image to be stored in a non-volatile memory based on the bio-signal and storing the sections of the acquired image in the non-volatile memory, wherein determining the sections of the acquired image to be stored in the non-volatile memory based on the at least one of the bio-signal or a vehicle signal comprises:
    calculating an individual score by assigning a weight for each item of the at least one of the heart rate, the electrocardiogram, the GSR, the body temperature, the voice, the facial expression, the stress level corresponding to items of the bio-signal, whether the vehicle has deviated a line, a vehicle speed, or a steering wheel angle corresponding to items of the vehicle signal;

determining an event time point, wherein a final score calculated by the individual score exceeds a threshold score; and determining the sections of the acquired image to be stored in the non-volatile memory based on the event time point.

13. The method of claim 12, further comprising acquiring the vehicle signal comprising whether the vehicle has deviated a line, the vehicle speed, or the steering wheel angle, wherein determining the sections of the acquired image to be stored in the non-volatile memory based on the bio-signal includes:

determining the sections of the acquired image to be stored in the non-volatile memory based on at least one of the bio-signal or the vehicle signal.

14. The method of claim 12, wherein determining the event time point includes determining the event time point, wherein the final score exceeds the threshold score and the calculated final score is not calculated only by the individual score of the item corresponding to the vehicle signal at the event time point.

15. The method of claim 12, wherein:

the weight assigned to the heart rate includes a greatest weight among weights assigned to the items of the bio-signal; and a weight assigned to the vehicle speed includes a greatest weight among weights assigned to the items of the vehicle signal.

16. The method of claim 12, wherein calculating the individual score includes calculating the individual score of the item including at least one of the heart rate, the electrocardiogram, the GSR, the body temperature, the voice, the facial expression, the stress level, whether the vehicle has deviated the line, the vehicle speed, or the steering wheel angle based on a change corresponding to the item within a predetermined time for each item.

17. The method of claim 12, wherein calculating the individual score includes calculating the individual score corresponding to an item of the facial expression when the facial expression is recognized as corresponding to a specific emotion.

18. The method of claim 12, wherein calculating the individual score includes calculating the individual score corresponding to an item of the voice when a specific word is recognized.

19. The method of claim 12, wherein determining the sections of the acquired image to be stored in the non-volatile memory based on the event time point includes determining sections respectively corresponding to specific times before and after the event time point as the sections to be stored in the non-volatile memory.

20. A device for recording an image for a vehicle, the device comprising:

an image acquisition device coupled configured to acquire an image of a region around the vehicle; and a sensor device configured to acquire a bio-signal of a driver, the bio-signal comprising a signal carrying information selected from the group consisting of a heart rate, an electrocardiogram, a galvanic skin response (GSR), a body temperature, a voice, a facial expression, and a stress level and combinations thereof;

a non-volatile memory; and a controller configured to:

determine sections of the acquired image to be stored in the non-volatile memory based on the bio-signal;

store the sections of the acquired image in the non-volatile memory;

determine an event time point, wherein a final score calculated through an individual score calculated by applying a weight for each of one or more items of the heart rate, the electrocardiogram, the GSR, the body temperature, the voice, the stress level corresponding to items of the bio-signal and whether the vehicle has deviated a line, a vehicle speed, and a steering wheel angle corresponding to items of a vehicle signal, exceeds a threshold score at the event time point; and determine the sections of the acquired image to be stored in the non-volatile memory based on the event time point.

* * * * *